United States Patent
Imran et al.

(10) Patent No.: US 9,968,795 B2
(45) Date of Patent: *May 15, 2018

(54) IMPLANTABLE NEUROSTIMULATOR DEVICES INCLUDING BOTH NON-RECHARGEABLE AND RECHARGEABLE BATTERIES AND METHODS OF USE THEREWITH

(71) Applicant: St. Jude Medical Luxembourg Holdings SMI S.A.R.L. ("SJM LUX SMI"), Luxembourg (LU)

(72) Inventors: Mir A. Imran, Los Altos, CA (US); Lynn Elliott, Maple Grove, MN (US)

(73) Assignee: ST. JUDE MEDICAL LUXEMBOURG HOLDINGS SMI S.A.R.L. ("SJM LUX SMI"), Plano, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/289,865

(22) Filed: Oct. 10, 2016

(65) Prior Publication Data

US 2017/0128733 A1 May 11, 2017

Related U.S. Application Data

(63) Continuation of application No. 14/606,795, filed on Jan. 27, 2015, now Pat. No. 9,463,320.
(Continued)

(51) Int. Cl.
*A61N 1/00* (2006.01)
*A61N 1/378* (2006.01)
(Continued)

(52) U.S. Cl.
CPC ......... *A61N 1/3787* (2013.01); *A61N 1/3605* (2013.01); *A61N 1/37223* (2013.01);
(Continued)

(58) Field of Classification Search
CPC ................ A61N 1/3787; A61N 1/3605; A61N 1/37223; A61N 1/37229; H02J 50/10; H02J 7/025; H04B 5/0031; H04B 5/0037
See application file for complete search history.

(56) References Cited

U.S. PATENT DOCUMENTS

| | | | | |
|---|---|---|---|---|
| 4,134,408 A | * | 1/1979 | Brownlee | ............ A61N 1/3787 607/33 |
| 7,813,801 B2 | * | 10/2010 | Youker | ................ A61N 1/3787 607/29 |
| 2010/0256708 A1 | * | 10/2010 | Thornton | ................ A61N 1/375 607/61 |

* cited by examiner

Primary Examiner — Mallika D Fairchild (57) ABSTRACT

An implantable neurostimulation (INS) device includes a non-rechargeable battery, a rechargeable battery, an antenna, an inductive coil, a neurostimulation module and a telemetry module. The neurostimulation module produces neurostimulation signals for delivery to target neural tissue, and the telemetry module wirelessly communicates with a non-implantable device using at least one of the antenna and the inductive coil. The non-rechargeable battery provides power to the neurostimulation module, and the rechargeable battery provides power to the telemetry module. The INS device also includes a charge module that charges the rechargeable battery in dependence on signals received from a non-implantable device via the inductive coil. Additional modules, such a sensor module, can be powered by the rechargeable battery. Additionally modules, such as controller, can be powered by the non-rechargeable battery. The rechargeable battery can power components normally powered by the non-rechargeable battery, when a capacity of the non-chargeable battery falls below a threshold.

14 Claims, 3 Drawing Sheets

Related U.S. Application Data (60) Provisional application No. 61/932,454, filed on Jan. 28, 2014.

(51) Int. Cl.
  *A61N 1/36* (2006.01)
  *H02J 50/12* (2016.01)
  *A61N 1/372* (2006.01)
  *H02J 5/00* (2016.01)
  *H02J 7/02* (2016.01)
  *H04B 5/00* (2006.01)
  *H02J 50/10* (2016.01)
  *H02J 7/00* (2006.01)
  *H02J 9/06* (2006.01)

(52) U.S. Cl.
  CPC .............. *H02J 5/005* (2013.01); *H02J 7/025* (2013.01); *H02J 50/10* (2016.02); *H02J 50/12* (2016.02); *H04B 5/0031* (2013.01); *H04B 5/0037* (2013.01); *H04B 5/0081* (2013.01); *H02J 7/0068* (2013.01); *H02J 9/06* (2013.01)

IMPLANTABLE NEUROSTIMULATOR DEVICES INCLUDING BOTH NON-RECHARGEABLE AND RECHARGEABLE BATTERIES AND METHODS OF USE THEREWITH

RELATED APPLICATIONS

This application is a continuation of U.S. patent application Ser. No. 14/606,795, filed Jan. 27, 2015, claims priority to U.S. Provisional Patent Application No. 61/932,454, filed Jan. 28, 2014, which are incorporated herein by reference.

FIELD OF THE INVENTION

Embodiments of the present invention generally pertain to implantable neurostimulator (INS) devices that include both a non-rechargeable battery and a rechargeable battery, and methods for use therewith.

BACKGROUND OF THE INVENTION

An electrically operated implantable neurostimulator (INS) device can be used, e.g., to stimulate a patient's spinal cord or brain to treat various disorders, including, but not limited to, pain or epileptic seizures. For example, neurostimulation delivered using an INS device has become an accepted treatment for patients with chronic pain in their back and/or limbs who have not found pain relief from other treatments. In general, such neurostimulation comprises applying an electrical current to nerve tissue in the pathway of the chronic pain. This creates a sensation that blocks the brain's ability to sense the previously perceived pain. An INS device can be a spinal cord stimulator (SCS) that treats chronic pain by delivering stimulation pulses to a patients spinal cord to induce paresthesia in regions of a patient's body that are afflicted by chronic pain. For a more specific example, an INS device can be used to selectively stimulate one or more target dorsal root ganglion (DRG), as disclosed in U.S. Pat. No. 7,450,993, entitled "Methods for Selective Stimulation of a Ganglion," which is incorporated herein by reference. Other types of INS devices deliver deep brain stimulation, cortical stimulation, cochlear nerve stimulation, peripheral nerve stimulation, vagal nerve stimulation, sacral nerve stimulation, and the like. Such INS devices are typically implanted in the upper buttock or abdomen (under the skin) of patient's, but are not limited thereto.

An electrically operated INS device needs a power source. Some electrically operated INS devices are powered by a primary cell (commonly referred to as a non-rechargeable battery). When the battery of such an INS device is depleted, the device must be explanted such that its battery can be replaced or a new INS device with a new battery can be implanted. Other electrically operated INS devices include secondary cells (commonly referred to as rechargeable batteries). The rechargeable battery of such an INS device can be recharged using a non-implanted device. For example, the INS device and the non-implanted device can include inductive coils that enable power to be wirelessly transferred, through a patient's skin, from the non-implanted device to the INS device for the purpose of charging the rechargeable battery.

Many electrically operated implantable neurostimulation devices are capable of communicating with a non-implanted device, such as a non-implanted clinician programmer and/or a non-implanted patient programmer. Such electrically operated INS devices and non-implanted programmers often include an antenna or an inductive coil that enables communication signals to be wirelessly transferred therebetween through a patient's skin.

SUMMARY OF THE INVENTION

Embodiments of the present invention generally pertain to INS devices, and methods for use therewith. In accordance with an embodiment, an INS device includes an antenna, an inductive coil, a neurostimulation module that produces neurostimulation signals for delivery to target neural tissue via one or more implantable leads, and a telemetry module that enables wirelessly communicates with a non-implantable device using at least one of the antenna and the inductive coil. Additionally, the INS device includes a non-rechargeable battery that provides power to the neurostimulation module, and a rechargeable battery that provides power to the telemetry module. The INS device also includes a charge module that charges the rechargeable battery in dependence a power signal received from a non-implantable device via the inductive coil.

In accordance with an embodiment, the telemetry module uses the antenna to wirelessly communicate with a non-implantable device. Additionally, the telemetry module uses the inductive coil to provide backup-communication with a non-implantable device and/or to initiate a communication session with a non-implantable device.

In an embodiment, the INS device includes a central processing unit (CPU) that receives or otherwise accesses stimulation data that defines the stimulation signals deliverable by the neurostimulation module via one or more implantable leads. The rechargeable battery provides power to the CPU when the CPU is in a low-power mode, and the non-rechargeable battery provides power to the CPU when the CPU is not in the low-power mode (i.e., when the CPU is in its normal power mode).

In an embodiment, the INS device also includes a sensor module that includes a sensor (e.g., an accelerometer) that detects at least one of motion or position. The rechargeable battery also provides power to the sensor module. The sensor module can also include an analog-to-digital converter (ADC) that converts an analog signal output by the sensor of the sensor module to a digital signal. The ADC is also powered by the rechargeable battery.

In an embodiment, the charge module that charges the rechargeable battery is capable of powering other modules of the implantable neurostimulation device while receiving, via the inductive coil, a power signal from a non-implantable device. Such a power signal can be modulated to have data embedded therein, in which case the power signal transferred between the inductive coil of the non-implantable device and the inductive coil of the INS is also a communication signal.

In an embodiment, a volume occupied by the rechargeable battery is between approximately 1% and 20% of a volume occupied by the non-rechargeable battery.

In an embodiment, an amp-hour rating of the rechargeable battery is between approximately 0.5% and 10% of an amp-hour rating of the non-rechargeable battery.

In an embodiment, the rechargeable battery is used to power modules that are normally powered by the non-rechargeable battery, when a capacity of the non-rechargeable battery falls below a specified threshold level.

This summary is not intended to be a complete description of the various embodiments of the present invention. Other features and advantages of the embodiments of the present invention will appear from the following description in which the preferred embodiments have been set forth in detail, in conjunction with the accompanying drawings and claims.

DETAILED DESCRIPTION

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

As mentioned above, most INS devices include and are powered by either a non-rechargeable battery or a rechargeable battery. An advantage of an INS device being powered by a non-rechargeable battery is that a non-rechargeable battery typically has much higher energy and power densities than a rechargeable battery. Additionally, the patient does not have to remember to, and be burdened to, periodically recharge a non-rechargeable battery. However, a disadvantage of an INS device being powered by a non-rechargeable battery is that when the non-rechargeable battery is depleted, the device must be explanted such that its battery can be replaced or a new INS device with a new battery can be implanted. An advantage of an INS device being powered by a rechargeable battery is that when the rechargeable battery is depleted, the battery can be recharged without explanting the INS device, potentially reducing how often the INS device must be explanted. Certain embodiments of the present invention, described herein, are directed to an INS device that includes both a non-rechargeable battery and a rechargeable battery in order to obtain the advantages of each type of battery and overcome the disadvantages of each type of battery. An example of such an INS device is shown in FIG. 1, which is described below.

Figure 1:
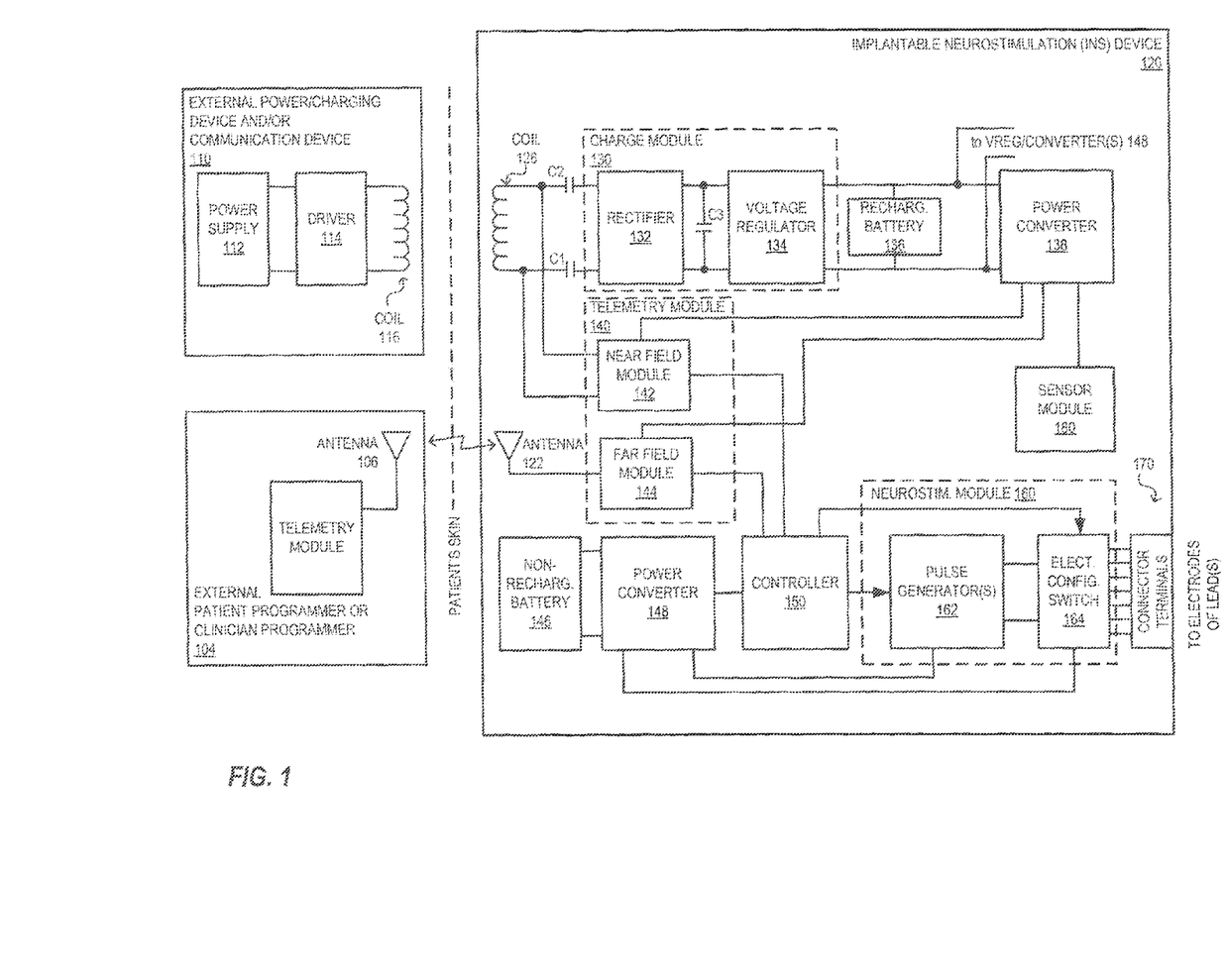
FIG. 1 illustrates an exemplary system including an electrically operated INS device that includes both a non-rechargeable battery and a rechargeable battery in accordance with an embodiment of the present invention.

Referring to FIG. 1, illustrated therein is a system that includes an INS device 120 that includes both a non-rechargeable battery 146 and a rechargeable battery 136. The INS device 120 is also shown as including an antenna 122, an inductive coil 126, a charge module 130, a power converter 138, a telemetry module 140, a power converter 148, a controller 150, a neurostimulation module 160, connector terminals 170, and a sensor module 180. The charge module 130 is shown as including a rectifier 132 and a voltage regulator 134. The rechargeable battery 136 can be, e.g., a lithium ion battery, but is not limited thereto. The INS device 120 is also shown as including coupling capacitors C1 and C2, which can also be referred to as DC blocking capacitors since they are used to block DC signals and pass AC signals.

The INS device 120 is capable of communicating with an external programmer 104 (that can be a clinician programmer or a patient programmer) using the antenna 122 of the INS device 120. Also shown in FIG. 1 is an external device 110 that includes an inductive coil 116 that can be inductively coupled to the inductive coil 126 of the INS device 120. As will be described in additional detail below, such an inductive coupling can be used to enable the INS device 120 to receive power from the external device 110, charge the rechargeable battery 136 of the INS device 120 and/or provide for communication (e.g., backup communication) with the external device 110.

The external programmer 104 can be used to program and/or adjust parameters of the INS device 120. The external programmer 104 includes an antenna 106 that is used to transmit wireless signals to, and/or receive wireless signals from, the antenna 122 of the INS device 120. In other words, the INS device 120 can perform wireless far field communication with the external programmer 104.

The INS device 120 can perform such wireless far field communication with the non-implantable device 104 using the Medical Implant Communication Service (MICS) standard, which was defined by the U.S. Federal Communications Commission (FCC) and European Telecommunications Standards Institute (ETSI). The MICS standard uses the RF band between 402 and 405 MHz to provide for bi-directional radio communication with implantable medical devices (IMDs), such as an INS device. The RF band between 402 and 405 MHz can be broken down into multiple channels, e.g., into ten 300 kHz wide channels, but not limited thereto. In 2009 the FCC began referring to the RF band between 402 and 405 MHz as being part of the 401 to 406 MHz Medical Device Radio communications (MedRadio) Service band. Accordingly, the RF band between 402 and 405 MHz can be referred to as the MICS/MedRadio band, and the communication standards relating to the MICS/MedRadio band can be referred to as the MICS/MedRadio communication standards. Alternatively, the INS device 120 can perform wireless RF communications with the non-implantable device 104 using the Industrial, Scientific and Medical (ISM) radio bands. The use of other standards and frequency bands are also possible. For example, the INS can perform wireless communication with a non-implantable device 104 using the wireless Bluetooth™ protocol standard, but is not limited thereto.

The external device 110, which can also be referred to as a non-implanted or non-implantable device, is shown as including a power supply 112, driver circuitry 114 and an inductive coil 116. The power supply 112 can be, for example, a battery or circuitry that converts AC power received from an AC power outlet to DC power. The driver circuitry 114 can be circuitry that drives the inductive coil 116 with an AC signal for the purpose of recharging, powering and/or communicating with the INS device 120. Accordingly, the driver circuitry 114 can, for example, include a DC-to-AC converter as well as communication circuitry. If used for communication, the driver 114 can be referred to as a telemetry module. While not specifically shown, the external device 110 can also include a controller, which can be part of or separate from the driver circuitry 114. Additionally, the external device 110 can include further components or modules, such as a user interface. Similarly, the external programmer 104 can include additional modules, such as a controller and a user interface. While shown as two separate devices, the external programmer 104 and the external device 110 can be implemented as a single external device that includes both an antenna and an inductive coil. Since embodiments of the present invention primarily relate to INS devices, not external devices, additional details of the external programmer 104 and the external device 110 are not provided. Further, it is noted that either of the devices 104 and 110 can be referred to as an external device, a non-implanted device or a non-implantable device.

The telemetry module 140 of the INS device 120 is shown as including a near field module 142 and a far field module 144. The near field module 142 can be a near field transceiver, a near field transmitter or a near field receiver. In other words, the near field module 142 enables near field wireless communication between the INS device 120 and the external device 110 using the inductive coil 126 of the INS device 120. To achieve such near field communication, the inductive coil 126 of the INS device 120 should be within a few centimeters of the inductive coil 116 of the external device 110. The far field module 144 can be a far field transceiver, a far field transmitter or a far field receiver. In other words, the far field module 144 enables far field wireless communication between the INS device 120 and the external device 104 using the antenna 122 of the INS device 120. To achieve such far field communication, the antenna 122 of the INS device 120 should be within a few meters of the antenna of the external programmer 104. Accordingly, far field communication can be achieved over a greater distance than near field communication, as the terms imply. Further, the far field communication provides for higher speed communication than the near field communication.

The near field module 142 and the far field module 144 are each coupled to the controller 150, either directly, via separate buses, via a shared telemetry data bus, or in some other manner. While shown as two separate blocks, the near field module 142 and the far field module 144 can share certain hardware and/or firmware. For example, while the near field module 142 and the far field module 144 may have their own hardware and/or firmware to implement their respective physical and data link layers, they may share hardware and/or firmware that are used to implement higher level communication protocol layers.

In accordance with an embodiment, the near field module 142 can be used to perform inductive near field communication in noisy RF environments, e.g., as a backup to the far field RF communication. Additionally, or alternatively, for security and/or authentication reasons, the near field module 142 can be used to perform inductive near field communication to initiate a communication session, and then the communication can be switched to the higher speed far field communication (performed using the far field module 144) for the remainder of the communication session, so long as the far field communication link quality is adequate.

The neurostimulation module 160 produces neurostimulation signals for delivery to target neural tissue via one or more implantable leads (not shown). The neurostimulation module 160 is shown as including one or more pulse generator(s) 162 that is/are configured to produce neurostimulation pulses, and more generally, neurostimulation signals. The pulse generator(s) 162 may include dedicated, independent pulse generators, multiplexed pulse generators or shared puke generators, which is/are controlled by the controller 150 via control signals to trigger or inhibit the neurostimulation pulses. The neurostimulation module 160 is also shown as including an electrode configuration switch 164.

The controller 150 can control the pulse generator(s) 162 to generate neurostimulation pulses, and control the electrode configuration switch 164 to couple the neurostimulation energy to selected electrodes of one or more selected leads. Additionally, the controller 150 can control the electrode configuration switch 164 to select different electrode configurations for delivery of stimulation energy from the pulse generator(s) 162. More specifically, the controller 150 can control the pulse generator(s) 162 and the electrode configuration switch 164 to deliver stimulation energy in accordance with selected neurostimulation parameters, which can specify a lead, an electrode configuration for the specified lead, and one or more pulse parameters, including, but not limited, pulse amplitude, pulse width and pulse repetition rate parameters. The controller 150 can include one or more of a microprocessor, a microcontroller, a digital signal processor (DSP), an application specific integrated circuit (ASIC), a field-programmable gate array (FPGA), a state machine, or similar discrete and/or integrated logic circuitry. The controller 150 can further include RAM or ROM memory, logic and timing circuitry and I/O circuitry. In accordance with a specific embodiment, the controller 150 is implemented using a microcontroller unit (MCU) that includes a central processing unit (CPU), memory, a direct memory access (DMA) controller, a clock system, a power controller, timers and input/output (I/O) ports, as described below with reference to FIG. 2. While not shown, the MCU may also include analog-to-digital converters (ADCs) and/or digital-to-analog converters (DACs).

The electrode configuration switch 164 can include a switch array, switch matrix, multiplexer, and/or any other type of switching device suitable to selectively couple connector terminals 170 of a connector (also known as a header) to the pulse generator(s) 162 and/or to sense circuitry (not shown in FIG. 1). The distal end(s) of one or more implantable neural stimulation leads (not specifically shown) can be connected to the connector.

In accordance with an embodiment, the non-rechargeable battery 146 provides power to the neurostimulation module 160 and the controller 150, and the rechargeable battery 126 provides power to the telemetry module 140 and the sensor module 180. This does not mean that the non-rechargeable battery 146 need be directly connected to the neurostimulation module 160 and the controller 150. Rather, as will be described below, a DC voltage produced by the non-rechargeable battery 146 can be regulated and/or converted to one or more other voltage level(s) that is are used to power the neurostimulation module 160 and the controller 150. Similarly, a DC voltage produced by the rechargeable battery 136 can be regulated and/or converted to one or more other voltage level(s) that is/are used to power the telemetry module 140 and the sensor module 180. A benefit of this configuration is that it takes advantage of the advantages of both the non-rechargeable battery 146 and the rechargeable battery 136. For example, if it is assumed that the telemetry module 140 and the sensor module 180 collectively consume X % (e.g., 10%) of the total power consumed by the neurostimulation module 160 and the controller 150 collectively, then this embodiment may increase the longevity of the INS device 120 by about X % (e.g., by about 10%), as compared to if all of the modules within the INS device 120 were powered by the non-rechargeable battery 146. Continuing with the assumption that the telemetry module 140 and the sensor module 180 collectively consume X % (e.g., 10%) of the total power consumed by the neurostimulation module 160 and the controller 150 collectively, then this embodiment will significantly reduce how often the rechargeable battery 136 of the INS device 120 needs to be recharged, as compared to if all of the modules within the INS device 120 were powered by the rechargeable battery 136.

The sensor module 180 can, e.g., include an accelerometer or some other sensor that detects motion and/or position, but is not limited thereto. Such a sensor may output an analog signal that is preferably converted to a digital signal that can be interpreted by the controller 150. According, the sensor module 180 may also include an analog-to-digital converter (ADC) that converts an analog signal to a digital signal at a specified sampling rate. In accordance with an embodiment, the rechargeable battery 136 powers both the sensor and the ADC of the sensor module 180.

As mentioned above, the inductive coil 126 of the INS device 120 can used for receiving power signals from the non-implanted device 110, as well as for receiving communication signals from the non-implanted device 110. More specifically, the inductive coil 126 of the INS device 120 enables near field coupling with the inductive coil 116 of the non-implanted device 110. When the non-implanted device 110 transmits a power signal by radiating RF power using its inductive coil, an inductive coupling between the inductive coil 116 of the non-implanted device 110 and the inductive coil 126 of the INS device 120 causes current to be induced in the inductive coil 126 of the INS device 120. This can more generally be referred to as the INS device 120 receiving the power signal. The received power signal, which is an AC signal, is rectified by the rectifier 132 of the charge module 130. The output of the rectifier 132, which can be referred to as a rectified signal, is smoothed by a capacitor C3 of the charge module 130, to produce a nearly DC voltage signal, albeit one with voltage ripple. This nearly DC voltage signal is provided to the voltage regulator 134, which outputs a substantially constant DC voltage signal. This substantially constant DC voltage signal, output by the voltage regulator 134, can be used to recharge the rechargeable battery 136. It is also possible that the substantially constant DC voltage signal, output by the voltage regulator 134, can be provided directly to the power converter 138.

A power signal emitted by the inductive coil 116 of the external device 110 to the inductive coil 126 of the INS device 120 may be distinct from a communication signal emitted by the inductive coil 116 of the external device 110 to the inductive coil 126 of the INS device 120. Alternatively, data can be embedded into the power signals emitted by the inductive coil 116 using any one of various different modulation schemes, in which case a signal emitted by the inductive coil 116 can be used for both transmitting data and recharging the rechargeable battery 136 of the INS 120. In other words, a power signal and a communication signal can be implemented using a same signal. It is also noted that depending upon implementation, it is possible that that inductive coils (e.g., 126 and 116) can be used for far field communications.

The power converter 138 receives a DC voltage from the rechargeable battery 136 (and/or from the voltage regulator 134) and, regulates, steps-up and/or steps-down this voltage to one or more voltage level(s) used for powering various other components of the INS device 120, including, but not limited to the telemetry module 140 and the sensor module 180. Accordingly, the power converter 138 can include voltage regulator circuitry and/or voltage conversion circuitry.

The power converter 148 receives a DC voltage from the non-rechargeable battery 146 and regulates, steps-up and/or steps-down this voltage to one or more voltage level(s) used for powering various other components of the INS device 120, including, but not limited to the controller 150 and the neurostimulation module 160. For example, the power converter 148 can provide a first voltage level to the controller 150, a second voltage level to the pulse generator(s) 162 and a third voltage level to the electronic configuration switch of 164 of the neurostimulation module 160, wherein one or more of the first, second and third voltage levels may or may not be the same, depending upon implementation. Accordingly, the power converter 148 can include voltage regulator circuitry and/or voltage conversion circuitry.

In certain embodiments, while the inductive coil 126 is receiving a signal transmitted by the inductive coil 116 of the external device 110, the power converter 138 (and/or the power converter 148) can receive a voltage output by the voltage regulator 134, in which case the power converter 138 (and/or the power converter 148) can power other modules of the INS device 120 while the rechargeable battery 136 is being recharged. This can be useful, for example, if the rechargeable battery 136 is allowed to be completely (or almost completely) depleted before a recharge is initiated. More specifically, this can allow for immediate communication between the external device 110 and the INS device 120, rather than needing to wait for the rechargeable battery 136 to be sufficient recharged before being able to provide for such communication.

Figure 2:
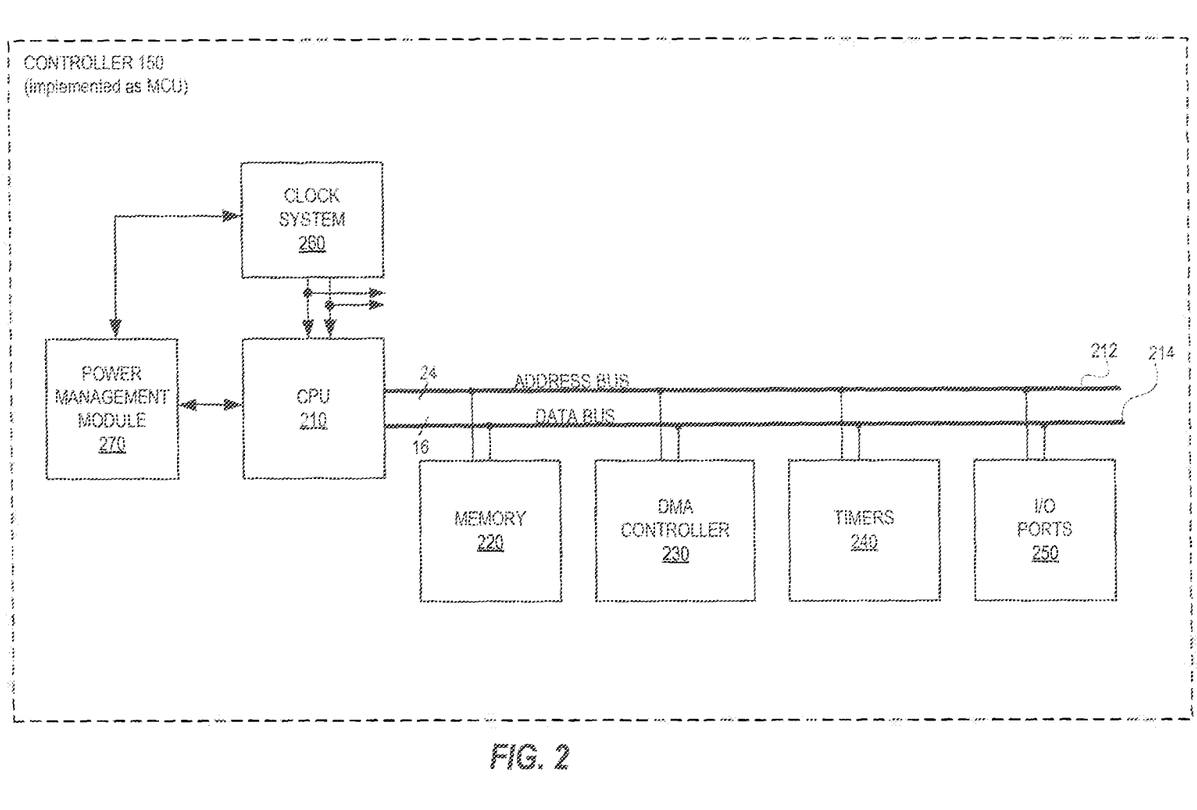
FIG. 2 illustrates exemplary details of the controller of the INS device introduced in FIG. 1, according to an embodiment.

As mentioned above, the controller 150 can be implemented using a microcontroller unit (MCU). An example of such an embodiment is illustrated in FIG. 2. Referring to FIG. 2, the controller 150 (implemented as a MCU) is shown as including a central processing unit (CPU) 210 connected to an address bus 212 and a data bus 214. Also connected to the address and data busses 212 and 214 are memory 220, a direct memory access (DMA) controller 230, timers 240 and input/output (I/O) ports 250. Also shown in FIG. 2 is a clock system 260 that can generate clock signals having different frequencies that can be provided to the CPU 210 and other components of the MCU and/or other modules of the INS device 120. The memory 220 can include volatile and/or non-volatile memory including, but not limited to, RAM, ROM, NVRAM, EEPROM, flash memory, and the like. Additionally, a power management module (PMM) 270 is shown, which can control when the CPU 210 enters low-power mode, and/or can control whether and when portions of the clock system 260 are at least partially disabled (to save power). Depending upon implementation, there are various different times that the CPU 210 may be switched from its normal power mode (i.e., not a low-power mode) to a low-power mode, and vise versa. For example, when the CPU 210 is in its normal power mode (i.e., not in a low-power mode), the CPU 210 may receive or otherwise access stimulation data that defines the stimulation signals deliverable by the neurostimulation module 160 via one or more implantable leads. Further, when the CPU 210 is in its normal power mode (i.e., not in a low-power mode), the CPU 210 may generate tables that are stored in the memory 220 and are used by the DMA controller 230 to control stimulation events. For a more specific example, the CPU 210 may generate and store in the memory 220, a first table that includes blocks of stimulation event data corresponding to stimulation events that are to be performed during a period of time (e.g., a 0.5 sec. or 1 sec. period of time), and a second table that includes blocks of next stimulation event time data corresponding to the period of time. After such tables are generated, the DMA controller 230 may use these tables to control the delivery of neurostimulation signals, thereby enabling the CPU 210 to be put into a low-power mode in order to conserve power. This is just one example of when the CPU 210 may be put into a low-power mode, which is not meant to be all encompassing, as there are various other reasons that the CPU 210 may be put into a low-power mode. In accordance with an embodiment, the rechargeable battery 136 provides power to the CPU 210 when the CPU 210 is in a low-power mode, and the non-rechargeable battery 146 provides power to the CPU 210 when the CPU 210 is not in the low-power mode, i.e., is in its normal power mode.

It is generally desirable that the INS device 120 be as small as possible, since it is implanted within a patient's body. Accordingly, it may not be practical for the rechargeable battery 136 and the non-rechargeable battery 146 to both be full sized batteries. Rather, in accordance with an embodiment, a volume occupied by the rechargeable battery 136 is between approximately 1% and 20% (e.g., is about 10%) of a volume occupied by the non-rechargeable battery 146. Further, since the rechargeable battery 136 is capable of being recharged, it need have an amp-hour rating as high as the non-rechargeable battery 146. Accordingly, in an embodiment, an amp-hour rating of the rechargeable battery 136 is between approximately 0.5% and 10% (e.g., is about 5%) of an amp-hour rating of the non-rechargeable battery 146.

In accordance with an embodiment, when a capacity of the non-rechargeable battery 146 falls below a specified threshold level, the rechargeable battery 136 can be used to power modules that are normally powered by the non-rechargeable battery 146. For example, a replacement indicator (e.g., an alarm and/or message sent to a non-implanted device) may be triggered when non-rechargeable battery 146 falls below a replacement indicator threshold. At that point, or within a short period thereafter, the non-rechargeable battery 146 may not have sufficient capacity, and/or may not be capable of producing a sufficient voltage, to power the modules it normally powers. To enable the patient/user to continue to receive the benefits of the neurostimulation therapy provided by the INS device 120, until a time that the patient/user is able to schedule an explant/implant procedure during which the INS device 120 is replaced (or at least its non-rechargeable battery is replaced), the rechargeable battery 136 can power modules normally powered by the non-rechargeable battery 146, such as, but not limited to, the neurostimulation module 160 and the controller 150.

Figure 3:
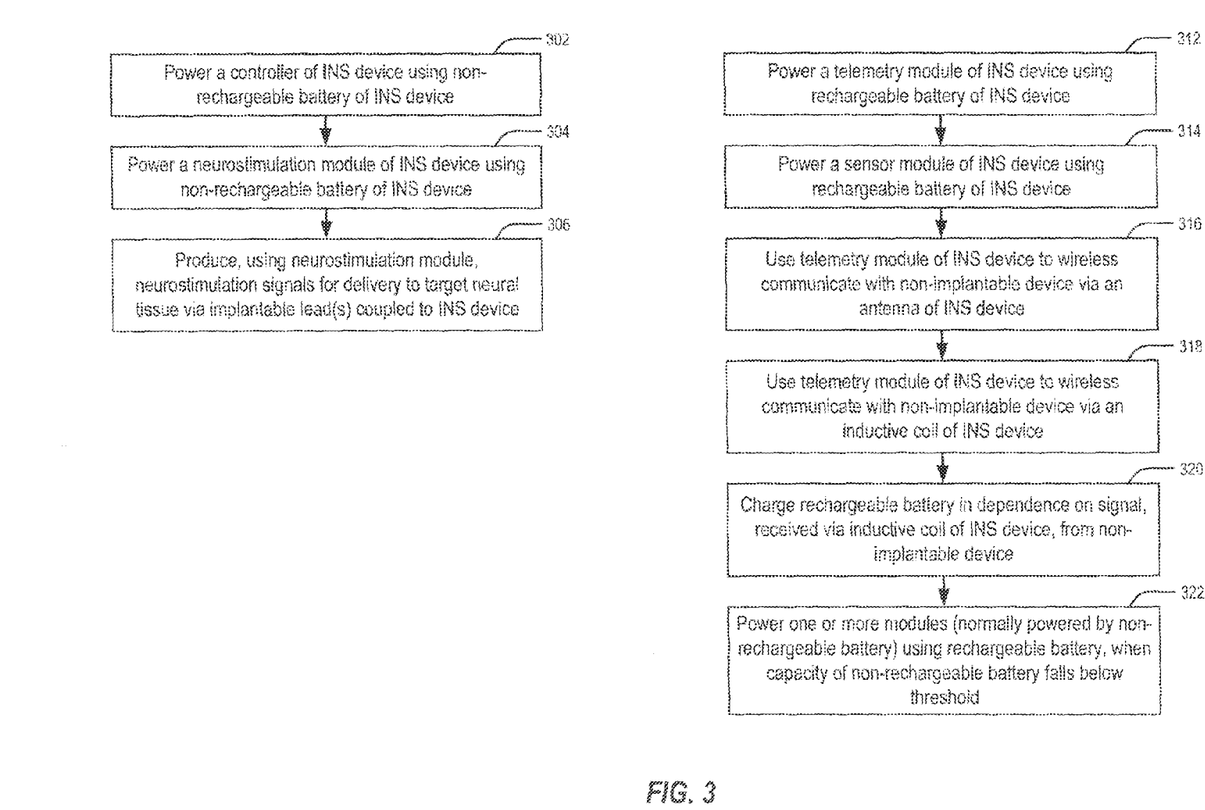
FIG. 3 is a high level flow diagram that is used to summarize a method according to an embodiment of the present invention.

FIG. 3 is a high level flow diagram that is used to summarize a method according to an embodiment of the present invention. The steps shown at the left in FIG. 3 are performed using power generated using a non-rechargeable battery (e.g., 146) of an INS device (e.g., 120) and/or using a module powered by the non-rechargeable battery of the INS device. The steps shown at the right in FIG. 3 are performed using power generated using a rechargeable battery (e.g., 136) of the INS device (e.g., 120) and/or using a module powered by the rechargeable battery of the INS device.

Referring to FIG. 3, at step 302, a controller (e.g., 150) of the INS device is powered using the non-rechargeable battery of the INS device. At step 304, a neurostimulation module (e.g., 160) of the INS device is powered using the non-rechargeable battery of the INS device. At step 306, the neurostimulation module is used to produce neurostimulation signals for delivery to target neural tissue via one or more implantable leads coupled to the INS device.

Still referring to FIG. 3, at step 312, a telemetry module (e.g., 140) of the INS device is powered using the rechargeable battery of the INS device. At step 314, a sensor module (e.g., 180) of the INS device is powered using the rechargeable battery of the INS device. At step 316, the telemetry module of the INS device is used to perform wireless communication with a non-implantable device (e.g., 104) via an antenna (e.g., 122) of the INS device. At step 318, the telemetry module of the INS device is used to perform wireless communication with a non-implantable device (e.g., 110) (which may or may not be the same non-implantable device referred to at step 316) via an inductive coil (e.g., 126) of the INS device. The communication performed at step 316, using the inductive coil, can be backup communication. Alternatively, or additionally, the communication performed at step 316, using the inductive coil, can be used to initiate a communication session, and then the antenna can be used for the remainder of the communication session. At step 320, the rechargeable battery is charged in dependence on a signal received via the inductive coil of the INS device from a non-implantable device (e.g., 110). At step 322, one or more modules (e.g., 160) (normally powered by the non-rechargeable battery) is/are powered using the rechargeable battery, when the capacity of the non-rechargeable battery (or an indicator of the capacity) falls below a corresponding specified threshold. Additional details of the steps described with reference to FIG. 3 can be appreciated from the above description of FIGS. 1 and 2, as can additional steps of a method.

Embodiments of the present invention have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 3. For another example, it is possible to change the boundaries of some of the blocks shown in FIGS. 1 and 2.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

The invention claimed is:

1. An implantable neurostimulation device, comprising:
   an antenna;
   an inductive coil;
   a neurostimulation module that produces neurostimulation signals for delivery to target neural tissue via one or more implantable leads;
   a telemetry module that wirelessly communicates with a non-implantable device using at least one of the antenna and the inductive coil;
   a non-rechargeable battery that provides power to the neurostimulation module;
   a rechargeable battery that provides power to the telemetry module during one or more periods of time that overlap with when the non-rechargeable battery provides power to the neurostimulation module, wherein the rechargeable battery supplements concurrent power of the non-rechargeable battery to provide power to the neurostimulation module when a capacity of the non-rechargeable battery falls below a specified threshold; and a charge module that charges the rechargeable battery in dependence power signals received from a non-implantable device via the inductive coil.

2. The implantable neurostimulation device of claim 1, wherein the telemetry module uses the antenna to wirelessly communicate with a non-implantable device.

3. The implantable neurostimulation device of claim 1, wherein the telemetry module uses the inductive coil to provide backup-communication with a non-implantable device or to initiate a communication session with a non-implantable device.

4. The implantable neurostimulation device of claim 1, further comprising: a central processing unit (CPU) that receives or otherwise accesses stimulation data that defines the stimulation signals deliverable by the neurostimulation module via one or more implantable leads; wherein the rechargeable battery provides power to the CPU when the CPU is in a low-power mode; and wherein the non-rechargeable battery provides power to the CPU when the CPU is not in the low-power mode.

5. The implantable neurostimulation device of claim 1, further comprising: a sensor module that includes a sensor that detects at least one of motion or position; wherein the rechargeable battery also provides power to the sensor module during one or more periods of time that overlap with when the non-rechargeable battery provides power to the neurostimulation module.

6. The implantable neurostimulation device of claim 5, wherein the sensor module also includes an analog-to-digital converter (ADC) that converts an analog signal output by the sensor of the sensor module to a digital signal, and wherein the ADC is also powered by the rechargeable battery during one or more periods of time that overlap with when the non-rechargeable battery provides power to the neurostimulation module.

7. The implantable neurostimulation device of claim 1, wherein the charge module that charges the rechargeable battery is capable of powering other modules of the implantable neurostimulation device while receiving, via the inductive coil, a signal from a non-implantable device.

8. The implantable neurostimulation device of claim 1, wherein: a volume occupied by the rechargeable battery is between 1% and 20% of a volume occupied by the non-rechargeable battery.

9. The implantable neurostimulation device of claim 1, wherein: an amp-hour rating of the rechargeable battery is between 0.5% and 10% of an amp-hour rating of the non-rechargeable battery.

10. A method for use by an implantable neurostimulation device, comprising:

powering a neurostimulation module of the implantable neurostimulation device using a non-rechargeable battery of the implantable neurostimulation device;

powering a telemetry module of the implantable neurostimulation device using a rechargeable battery of the implantable neurostimulation device during one or more periods of time that overlap with when the non-rechargeable battery is used for powering the neurostimulation module;

supplementing concurrent power of the non-rechargeable battery with power from the rechargeable battery to provide power to the neurostimulation module when a capacity of the non-rechargeable battery falls below a specified threshold;

producing, using the neurostimulation module, neurostimulation signals for delivery to target neural tissue via one or more implantable leads coupled to the implantable neurostimulation device; and wirelessly communicating with a non-implantable device using at least one of an antenna and an inductive coil connected to the telemetry module of the implantable neurostimulation device.

11. The method of claim 10, further comprising: charging the rechargeable battery based on a signal, received via the inductive coil of the implantable neurostimulation device, from a non-implantable device.

12. The method of claim 10, further comprising:

using a central processing unit (CPU) to receive or otherwise access stimulation data that defines the neurostimulation signals deliverable by the neurostimulation module via one or more implantable leads; powering the CPU using the rechargeable battery, when the CPU is in a low-power mode; and powering the CPU using the non-rechargeable battery, when the CPU is not in the low-power mode.

13. The method of claim 10, further comprising: powering a sensor module using the rechargeable battery, wherein the sensor module is used to detect at least one of motion or position during one or more periods of time that overlap with when the non-rechargeable battery is used for powering the neurostimulation module.

14. The method of claim 10, wherein: a volume occupied by the rechargeable battery is between 1% and 20% of a volume occupied by the non-rechargeable battery; and an amp-hour rating of the rechargeable battery is between 0.5% and 10% of an amp-hour rating of the non-rechargeable battery.

* * * * *